(12) United States Patent
Warren

(10) Patent No.: US 6,547,851 B2
(45) Date of Patent: Apr. 15, 2003

(54) MINIATURIZED WEARABLE OXYGEN CONCENTRATOR

(75) Inventor: John Lee Warren, Salmon Arm (CA)

(73) Assignee: Wearair Oxygen Inc., Kelowna (CA)

( * ) Notice: Subject to any disclaimer, the term of this patent is extended or adjusted under 35 U.S.C. 154(b) by 0 days.

(21) Appl. No.: 09/921,863

(22) Filed: Aug. 2, 2001

(65) Prior Publication Data

US 2002/0033095 A1 Mar. 21, 2002

Related U.S. Application Data

(60) Provisional application No. 60/222,591, filed on Aug. 2, 2000.

(51) Int. Cl.[7] ............................................. B01D 53/047
(52) U.S. Cl. ................................ 95/21; 95/98; 95/130; 96/114
(58) Field of Search ............................... 95/11, 19, 21, 95/96, 98, 103, 130; 96/109, 110, 113, 114, 115, 121

(56) References Cited

U.S. PATENT DOCUMENTS

| | | | |
|---|---|---|---|
| 2,944,627 A | 7/1960 | Skarstrom | .................. 183/4.7 |
| 3,400,713 A | 9/1968 | Finan | |
| 4,222,750 A * | 9/1980 | Gauthier et al. | ............... 95/102 |
| 4,516,424 A * | 5/1985 | Rowland | ..................... 73/1.06 |
| 4,685,939 A | 8/1987 | Kratz et al. | |
| 4,802,899 A * | 2/1989 | Vrana et al. | ................... 96/109 |
| 5,104,426 A * | 4/1992 | Yamada et al. | ................ 95/102 |
| 5,122,164 A * | 6/1992 | Hirooka et al. | ................ 95/130 |
| 5,340,381 A * | 8/1994 | Vorih | ........................... 95/105 |
| 5,529,607 A * | 6/1996 | Tan | ............................... 95/100 |
| 5,531,807 A | 7/1996 | McCombs | |
| 5,540,758 A * | 7/1996 | Agrawal et al. | ............... 95/101 |
| 5,850,833 A | 12/1998 | Kotliar | |
| 5,871,564 A | 2/1999 | McCombs | |
| 5,912,426 A * | 6/1999 | Smolarek et al. | .............. 96/115 |
| 5,968,233 A * | 10/1999 | Rouge et al. | .................. 95/101 |
| 6,003,744 A | 12/1999 | Culjak | |
| 6,238,458 B1 * | 5/2001 | Monereau | ..................... 95/101 |

* cited by examiner

Primary Examiner—David A. Simmons
Assistant Examiner—Frank M. Lawrence
(74) Attorney, Agent, or Firm—Anthony C. Edwards

(57) ABSTRACT

A component gas concentrator includes an air compressor, an air-tight first container containing a molecular sieve bed, the first container in fluid communication with the compressor through a first gas conduit, and an air-tight second container in fluid communication with the first container through a second gas conduit. A gas flow controller such as PLC controls actuation of valves mounted to the gas conduits.

30 Claims, 15 Drawing Sheets

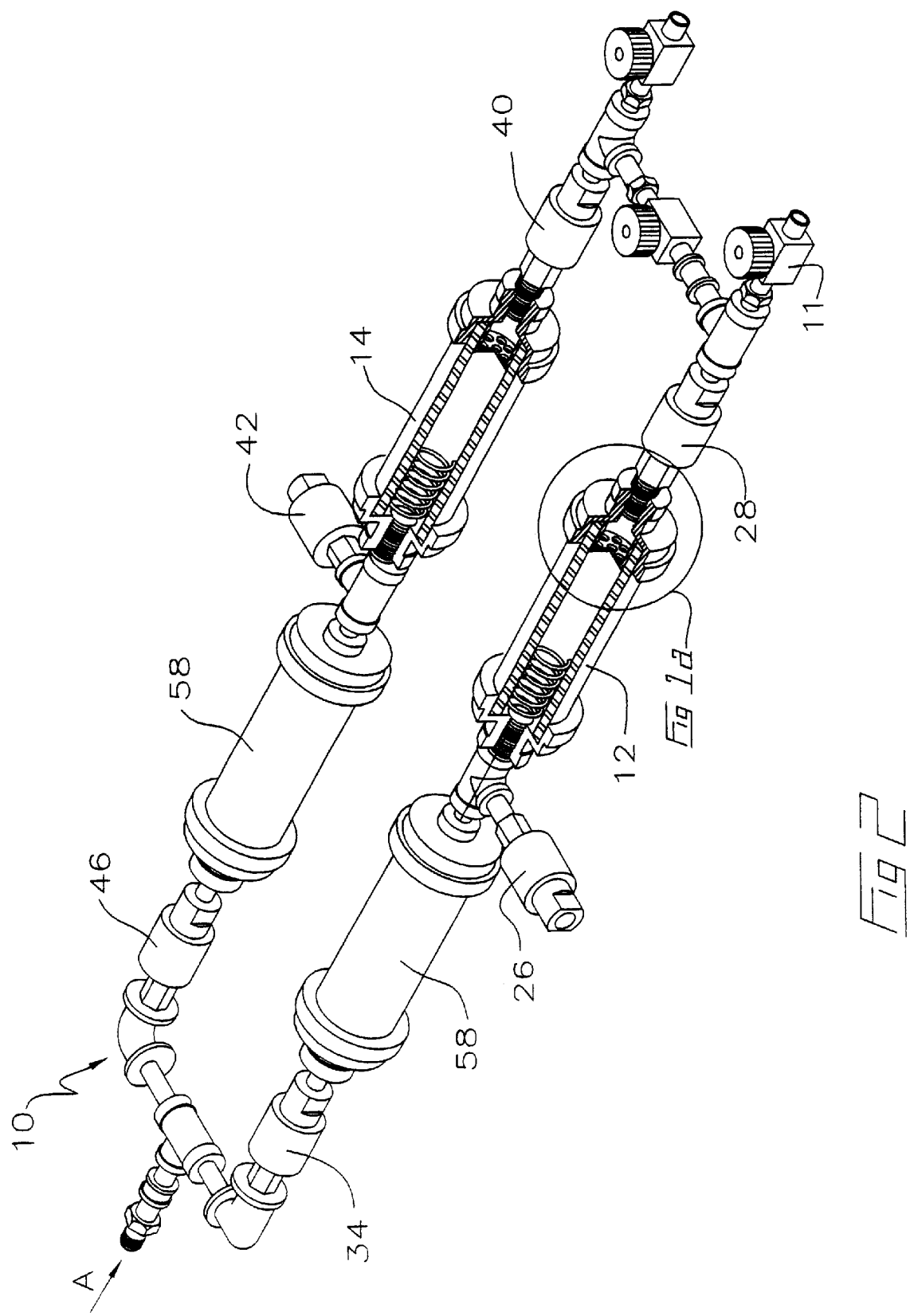

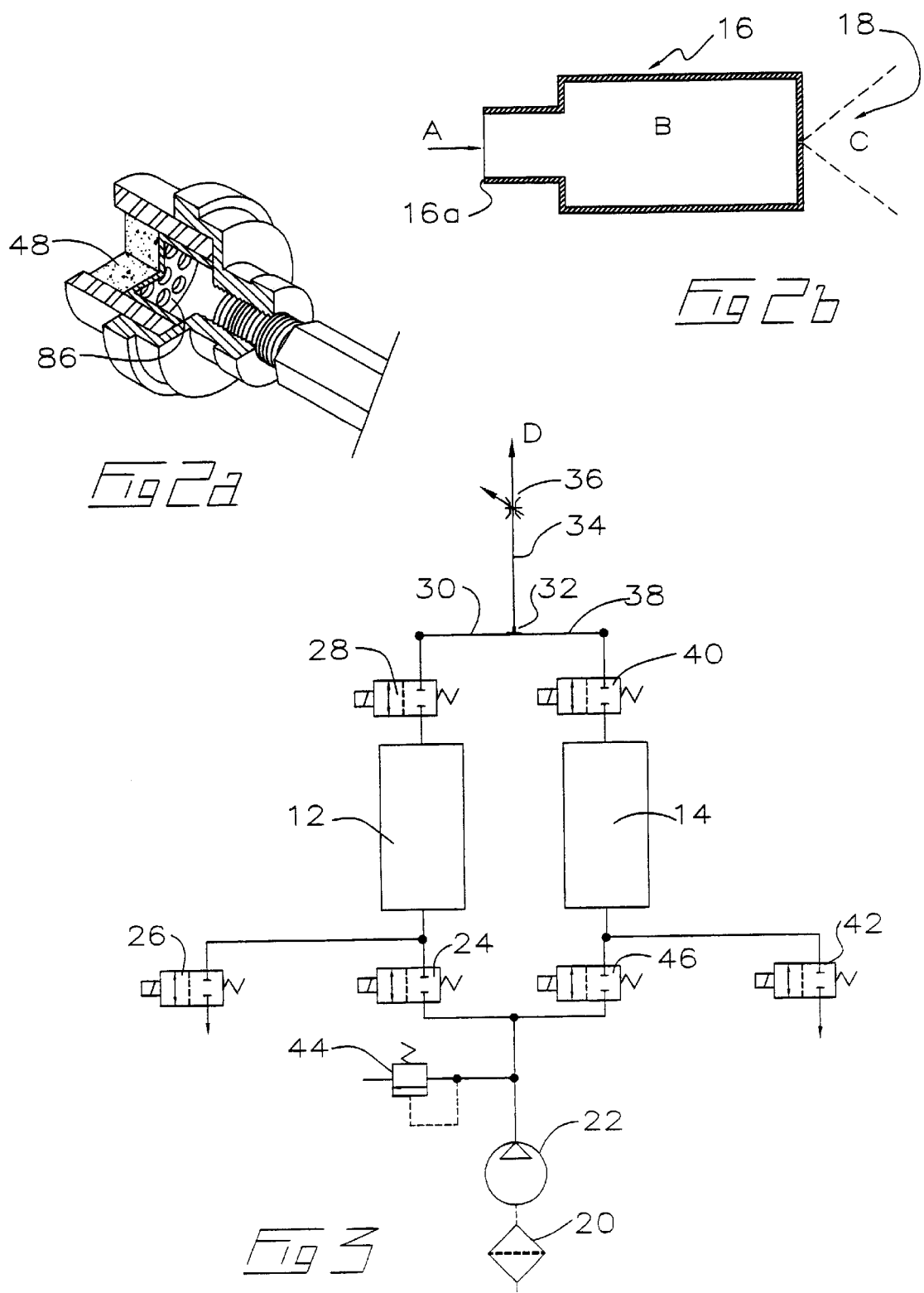

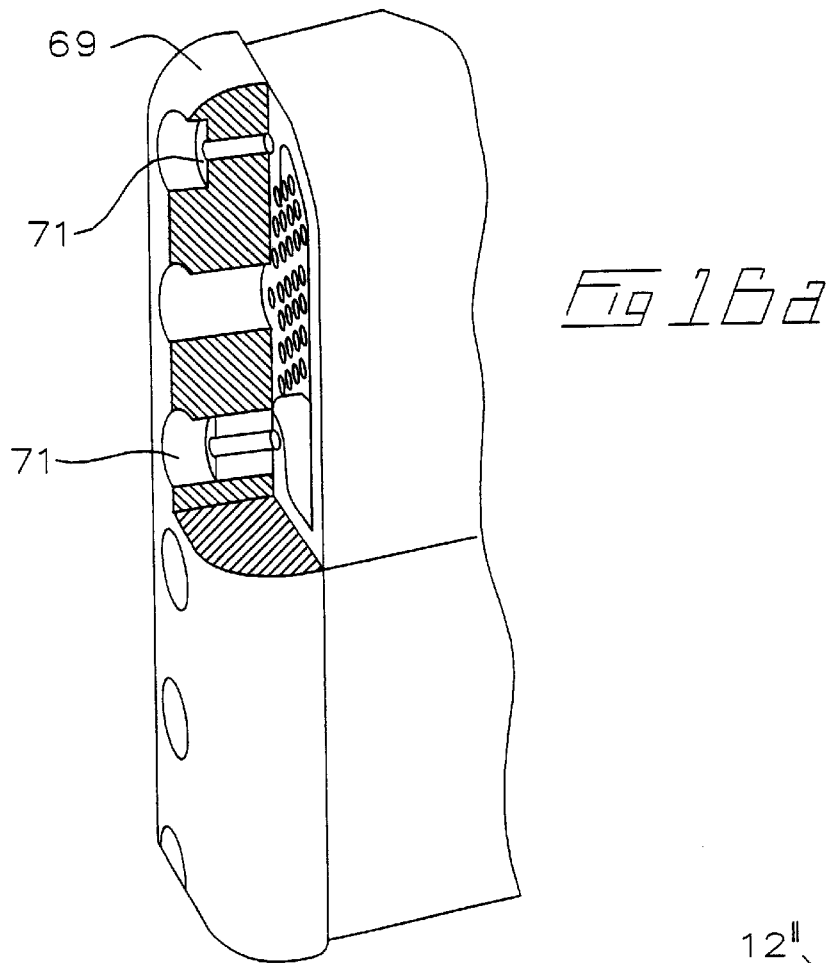
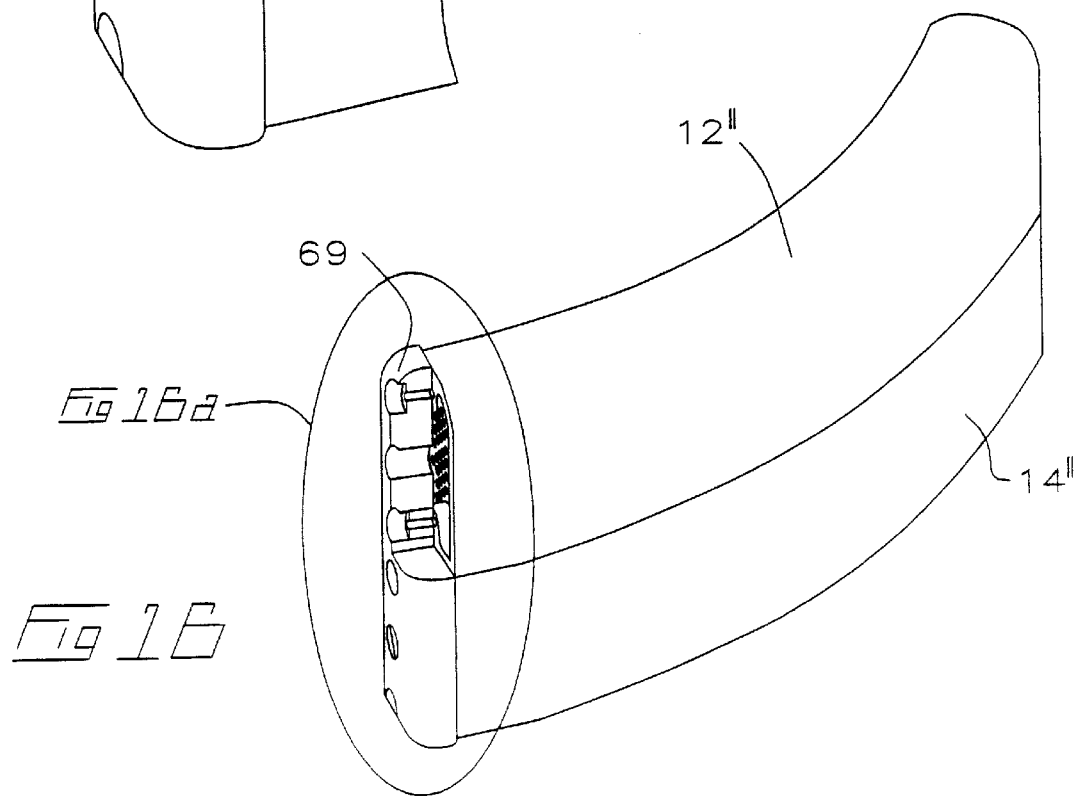

MINIATURIZED WEARABLE OXYGEN CONCENTRATOR

CROSS REFERENCE TO RELATED APPLICATION

This application claims priority from United States Provisional Patent Application No. 60/222,591 filed Aug. 2, 2000 entitled Portable Oxygen Concentrator.

FIELD OF THE INVENTION

This invention relates to the field of gas concentrators, and in particular to a miniaturized, portable gas concentrator and method of miniaturized gas concentration.

BACKGROUND OF THE INVENTION

The pressure swing adsorption cycle was developed by Charles Skarstrom. FIGS. 1A and 1B describe the operation of the Skarstrom "Heatless Dryer". In particular, ambient humid air is drawn into the system from an intake port, by a compressor. The pressurized air flows from the compressor through conduit 9 to a switching valve 4. With the valve in the shown position in FIG. 1A, pressurized air passes through conduit 5a to a pressure vessel 6a. The air feeds into the pressure vessel to a flow-restrictive orifice 1a. The effect of the restrictive orifice is to restrict the flow of gas escaping the pressure vessel. As the pressure builds up in the pressure vessel, water vapour condenses on the sieve material 8. Air with reduced humidity passes through orifice 1a to conduit 12. At conduit junction 11, some of the air is extracted for use from gas extraction port 2 while the remainder passes through conduit 13 to restrictive orifice 1b. The less humid air that passes through orifice 1b is used to blow humid air out of the unpressurized vessel 6b, through conduit 5b, through valve 4, to a vent port 7. When valve 4 switches to the position as shown in FIG. 1B, the opposite cycle occurs.

Thus, as valve 4 cycles from the position of FIG. 1A to the position of FIG. 1B, cyclically, there is a gradual reduction of humidity in the air as sampled at port 2. Likewise gases can be separated by adsorbing components of the gas on selective molecular sieves.

From laboratory observations, employing the Skarstrom cycle in the context of an oxygen separator or concentrator, wherein nitrogen is absorbed by molecular sieve beds to incrementally produce oxygen-enriched air, and using a precursor to the concentrator 10 arrangement of FIG. 2, it was observed that miniaturized (in this case nominal ¾ inch NPT pipe×6 inch long) molecular sieve beds 12 and 14 could only reach a maximum of 30% concentrated or enriched oxygen detected at the gas extraction ports 11. It was thought that this was because the control valve of the laboratory arrangement was switching before all the nitrogen could be vented out of the molecular sieve beds and the exhaust lines. However, measurements from these places showed that the oxygen concentration was higher than normal. Therefore this was not the problem.

It was also observed that there was a lot of air flow coming out of the molecular sieve bed before the molecular sieve bed was completely pressurized. It seemed that the molecular sieve bed was saturated with nitrogen before the bed was finished pressurizing. FIG. 2B diagrammatically represents such a molecular sieve bed 16. Compressed air enters the bed in direction A through inlet passage 16a. A volume of air B is contained within the bed cavity. A proportion of the volume of air C escapes out through an outflow needle valve 18 while the molecular sieve bed pressurizes. It was thought that the volume of air C escaping could be a much larger volume than the volume of air B inside the bed 16. Thus the question became, what happens when the volume of the molecular sieve bed is decreased during miniaturization, but everything else stays the same?

Poiseauille's Law was used in comparing the old bed volume B to the miniaturized bed volume to calculate the flow of a fluid that passes through a small hole such as needle valve 18 under a pressure difference.

$$1) \; Q = \frac{r^A (p_{InsideBed} - p_{OutsideBed})}{8 \eta L}$$

Where "Q" is the fluid flow in meters cubed per second. "r" is the radius of the small hole. "$p_{IsideBed} - p_{OutsideBed}$" is equal to the pressure difference between inside the molecular sieve bed and outside the molecular sieve bed. "$\eta$" is the fluid viscosity, and "L" is the depth of the small hole.

The flow rate, Q, in meters per second multiplied by the time the flow rate occurred is equal to the volume of flow in meters cubed.

$$2) \; V = Qt$$

The variable for Q in equation 1 in this case is constant so $$3) \; V = Kt$$

where K is some constant value.

Using this information to create a comparison of the Flows and Volumes of the original oxygen concentrator's bed volume to the new bed volume may be described as.

$$4) \; R = \frac{\frac{V_{FlowNew}}{V_{BedVolumeNew}}}{\frac{V_{FlowOld}}{V_{BedVolumeOld}}}$$

Since the time to pressurize the molecular sieve bed can be accurately timed using a programmable logic controller (PLC) timer, the following can be stated:

$$5) \; R = \frac{\frac{Kt_{New}}{V_{BedVolumeNew}}}{\frac{Kt_{Old}}{V_{BedVolumeOld}}} \; or$$

$$6) \; R = \frac{Kt_{New} V_{BedVolumeOld}}{Kt_{Old} V_{BedVolumeNew}} = \frac{t_{New} V_{BedVolumeOld}}{t_{Old} V_{BedVolumeNew}}$$

The ratio may then be calculated by inserting values using representative values for a prior art bed and a miniaturized bed (in this case ¾ inch NPT×6 inch long). Thus, for example:

$$7) \; R = \frac{(1)(0.001885741)}{(7)(0.0000434375)} = 6.2$$

From this it was concluded that the molecular sieve material of a nominal ¾ inch NPT pipe×6 inch long molecular sieve bed (the example used in equation 7) has approximately 6.2 times the air passing through it during its pressurization cycle than the molecular sieve material of a prior art oxygen concentrator during its pressurization cycle.

As a consequence of the findings of this analysis it was found to be advantageous to pressurize and vent the molecular sieve beds in a different way than the prior art pressure swing adsorption (PSA) technique. In the method of the present invention the bed is not vented until the bed is substantially fully pressurized, hereinafter referred to as an air packet system or method.

SUMMARY OF THE INVENTION

In summary, the gas, such as oxygen, concentrator of the present invention for enriching a target component gas concentration, such as the oxygen concentration, and minimizing a waste component gas concentration, such as the nitrogen concentration, in a gas flow, includes an air compressor, an air-tight first container containing a molecular sieve bed for adsorbing the waste component gas, the first container in fluid communication with the compressor through a first gas conduit, and an air-tight second container in fluid communication with the first container through a second gas conduit. A gas flow controller such as PLC controls actuation of valves mounted to the gas conduits. The valves regulate air flow through the conduits so as to sequentially, in repeating cycles:

(a) prevent gas flow between the first and second containers and to allow compressed gas from the compressor into the first container during a first gas pressurization phase, whereby the first container is pressurized to a threshold pressure level to create a gas packet having an incrementally enriched target component gas concentration such as incrementally enriched oxygen-enriched air;

(b) prevent gas flow into the first container from the compressor and allow gas flow from the first container into the second container during a gas packet transfer phase, wherein the gas packet is transferred to the second container;

(c) prevent gas flow into the second container from the first container and allow gas to vent to atmosphere out from the first container through a vent valve of the first container;

(d) allow gas flow between the first and second containers from the second container into the first container during an air packet counter-flow phase, wherein the gas packet flows from the second container to the first container; and, (e) prevent gas flow venting from the first container through the vent valve of the first container.

A gas flow splitter is mounted to the second gas conduit for diverting a portion of the gas packet into a gas line for delivery of target component gas, such as oxygen, enriched air for an end use, including use by an end user, downstream along the gas line.

In one embodiment of the present invention, both the first and second containers contain molecular sieve beds for adsorbing the waste component gas, in which case the second container is also in fluid communication with the compressor; for example through a third conduit. Also, in that case, the gas flow controller, following the air packet transfer phase and following preventing gas flow into the second container from the first container, allows compressed gas from the compressor into the second container during a second gas pressurization phase, whereby the second container is pressurized to the threshhold pressure level. The gas flow controller, following preventing the gas flow from venting from the first container through the vent valve of the first container and following preventing gas flow between the first and second containers during the first gas pressurization phase, allows gas to vent to atmosphere out from the second container through a vent valve of the second container and prevents gas flow into the second container from the compressor.

The gas flow controller may be a processor cooperating with the compressor so as to shut off the compressor when gas flow from the compressor into both the first and second containers is prevented. The processor and the compressor may be powered by a battery. The first and second containers, the conduits, the valves, the processor, the compressor and the battery may be mounted in a housing.

The first and second containers may be elongate hollow conduits. The molecular sieve beds may, where the waste component gas is nitrogen, include Zeolite as the molecular sieve material. The first and second containers may be generally parallel and mounted in the housing in parallel array. They may be spaced apart laterally relative to the length of the containers so as to define a channel therebetween. The processor and the compressor may be mounted in the channel. A valve and manifold housing may also be mounted in the channel, the valves mounted to the valve and manifold housing. The valve and manifold housing includes interconnecting manifolds for interconnecting the valves to the first and second containers and the compressor via the gas conduits.

A gas reservoir may be provided, for example formed as part of the valve and manifold housing, in fluid communication with the gas flow splitter. The reservoir is for containing a reserve of, for example, the oxygen-enriched air for delivery to the end use. One of the valves is a demand valve cooperating between the gas line and the reservoir for release of the reserve into the gas line upon a triggering event triggering actuation of the demand valve. In one embodiment, a pressure sensor cooperates with the gas line, and the triggering event is a drop in pressure in the gas line sensed by the pressure sensor. The pressure sensor provides a triggering signal to trigger the actuation of the demand valve upon detecting the drop in pressure, for example to a pre-set lower threshold pressure, below which the pressure sensor provides the triggering signal.

In one embodiment, the compressor is run intermittently upon actuation signals from the processor so as to only run when required, including during the pressurization phase.

In the embodiments in which the end use is for example oxygen supply to an end user such as a patient, the first and second containers may be elongate and curved along their length so as to conform to a body shape of the end user when the gas concentrator is worn by the end user. In any event, when the end use is oxygen supply to an end user, it is intended that the gas concentrator may be adapted to be worn by the end user.

Thus the method of the present invention includes the sequential steps, in repeating cycles, of:

(a) preventing gas flow between the first and second containers and allowing compressed gas from the compressor into the first container during a first gas pressurization phase, whereby the first container is pressurized to a threshold pressure level to create a gas packet having incrementally enriched target component gas concentration;

(b) preventing gas flow into the first container from the compressor and allowing gas flow from the first container into the second container during a gas packet transfer phase, wherein the gas packet is transferred to the second container;

(c) preventing gas flow into the second container from the first container and allowing gas to vent to atmosphere out from the first container through a vent valve of the first container;

(d) allowing gas flow between the first and second containers from the second container into the first container during an air packet counter-flow phase, wherein the gas packet flows from the second container to the first container; and, (e) preventing gas flow venting from the first container through the vent valve of the first container.

Where the gas concentrator further includes a molecular sieve bed for adsorbing the waste component gas in the second container and wherein the second container is in fluid communication with the compressor through a third conduit, the method of the present invention further includes the steps of:

(a) following the gas packet transfer phase and following preventing gas flow into the second container from the first container, the gas flow controller allowing compressed gas from the compressor into the second container during a second gas pressurization phase, whereby the second container is pressurized to the threshold pressure level; and (b) following preventing the gas flow from venting from the first container through the vent valve of the first container and following preventing gas flow between the first and second containers during the first gas pressurization phase, the gas flow controller allowing gas to vent to atmosphere out from the second container through a vent valve of the second container and preventing gas flow into the second container from the compressor.

BRIEF DESCRIPTION OF THE DRAWINGS

FIG. 2 is, in perspective view, a prototype embodiment of the oxygen concentrator of the present invention.

FIG. 2a is, in partially cut-away enlarged view, one end of a molecular sieve bed of FIG. 2.

FIG. 2b is a diagrammatic view of a singular molecular sieve bed having an uncontrolled outlet orifice such as would be found in the prior art pressure swing adsorption method.

FIG. 3 is a block diagram of one embodiment of the oxygen concentrator of the present invention.

FIG. 9 is, in end-on perspective view, a housing according to one embodiment of the oxygen concentrator of the present invention.

FIG. 16 is, in partially cut-away perspective view, a further embodiment of the molecular sieve beds of the oxygen concentrator of the present invention.

FIG. 16a is, in partially cut-away enlarged view, one end of the molecular sieve beds of FIG. 16.

DETAILED DESCRIPTION OF EMBODIMENTS OF THE INVENTION

Figure 1B:
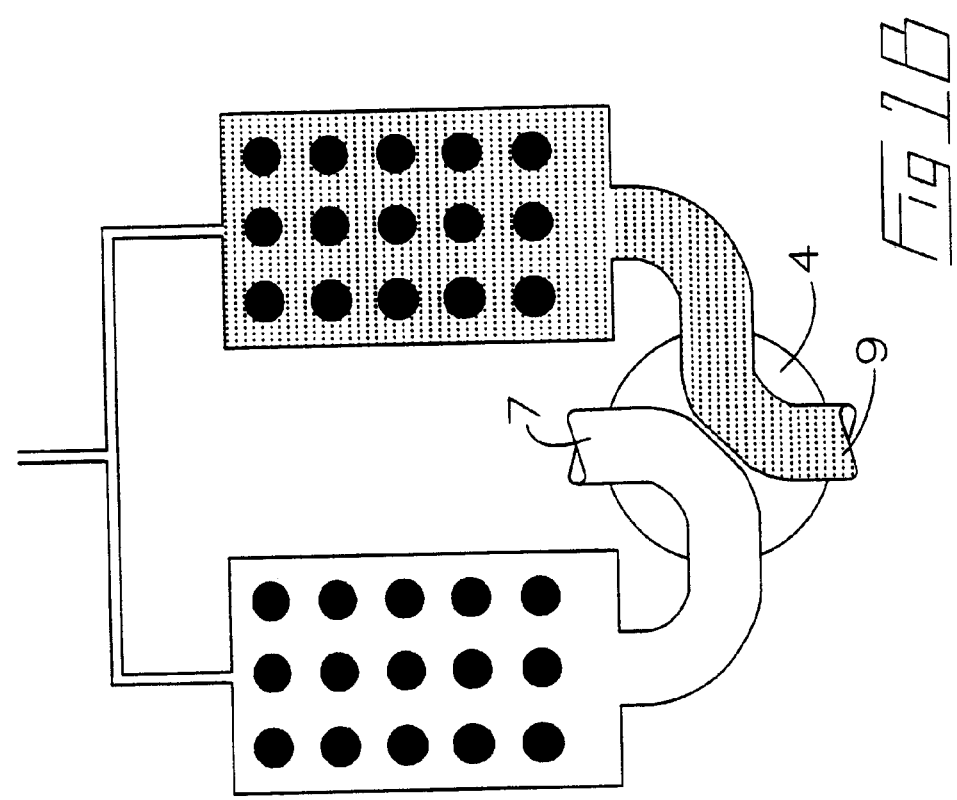
FIGS. 1A and 1B illustrate the Skarstrom Heatless Air Drying Device.

With reference to the accompanying figures in which like parts have the same reference numerals in each view, details of the concentration process and apparatus of the present invention are now provided. As used herein, including as used in the claims set out below, all references to oxygen and oxygen-enriched are intended to include other end-use gases which may be advantageously used in any end use once separated or concentrated according to the present invention from a parent gas (for example ambient air) comprising the end-use gas (for example oxygen) and waste gases (for example nitrogen) which may be adsorbed by a molecular sieve bed.

Figure 10:
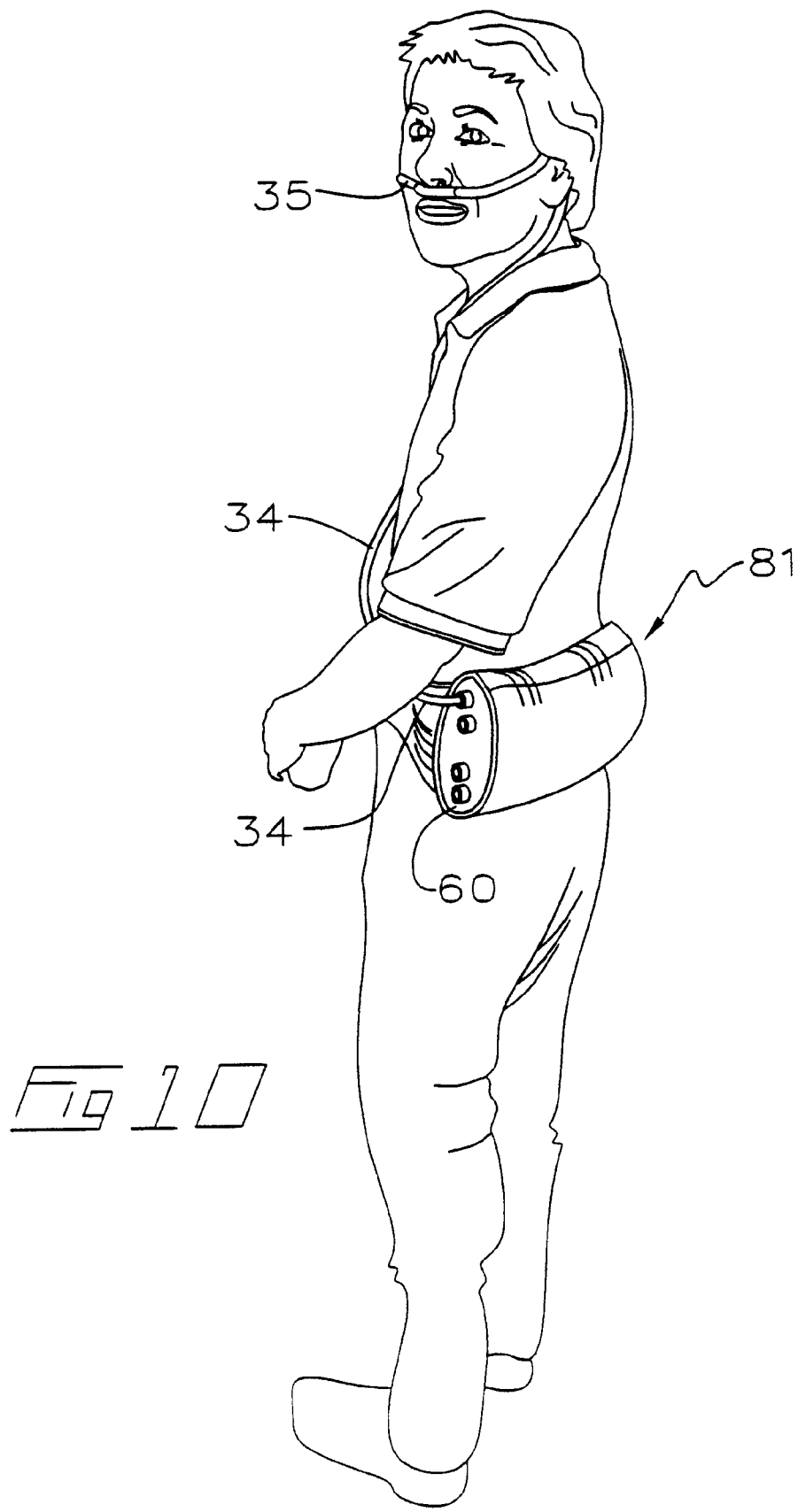
FIG. 10 is, in perspective view, an end user wearing an oxygen concentrator according to one embodiment of the present invention.

As can also be seen in FIG. 3 which is a diagrammatic illustration of an arrangement implementing the oxygen concentrator of the present invention, air is filtered through intake filter 20 and is pressurized by compressor 22. The air stream is directed to pressurize bed 12 by having a supply valve 24 for bed 12 open and a nitrogen vent 26 for bed 12 closed. Control valve 28 is closed so that bed 12 pressurizes without any air venting. Valves 24, 26 and 28 may be solenoid valves. When bed 12 is pressurized, for example to 10 psi, then supply valve 24 is closed so that no more air enters into bed 12. At the same time control valve 28 is opened for a time to allow oxygen-enriched air to flow through air conduit 30 and the through air flow splitter 32 so as to split a percentage of the air flow through a gas extraction port and air flow conduit 34 so as to supply oxygen-enriched air to an end us at the end of conduit 34 such as a patient breathing the oxygen-enriched air flow. Conduit 34 supplies flow in direction D to an end-use (such as machine requiring or using oxygen-enriched air) or an end-user (such as seen in FIG. 10) through a needle valve 36. The remainder of the airflow continues through conduit 38 through open control valve 40 into bed 14 so as to be contained therein. Oxygen-enriched air that flows into bed 14 to purge the bed of nitrogen, vents out through the nitrogen vent 42. In an embodiment where the compressor is not turned on and off to preserve battery life, while bed 12 is generating oxygen-enriched air, pressure relief valve 44 may be venting air from compressor 22 unless the compressor is being run intermittently on a demand-based basis as better described below. Pressure may be relieved by the use of PLC time-controlled solenoid valves or pressure relief valves. It has been found advantageous to use 10 Angstrom Zeolite for example Oxi-sive 5 (13x)™ Zeolite marketed by OUP in Calgary, Alberta, Canada, although other forms of Zeolite will also work.

Figure 4:
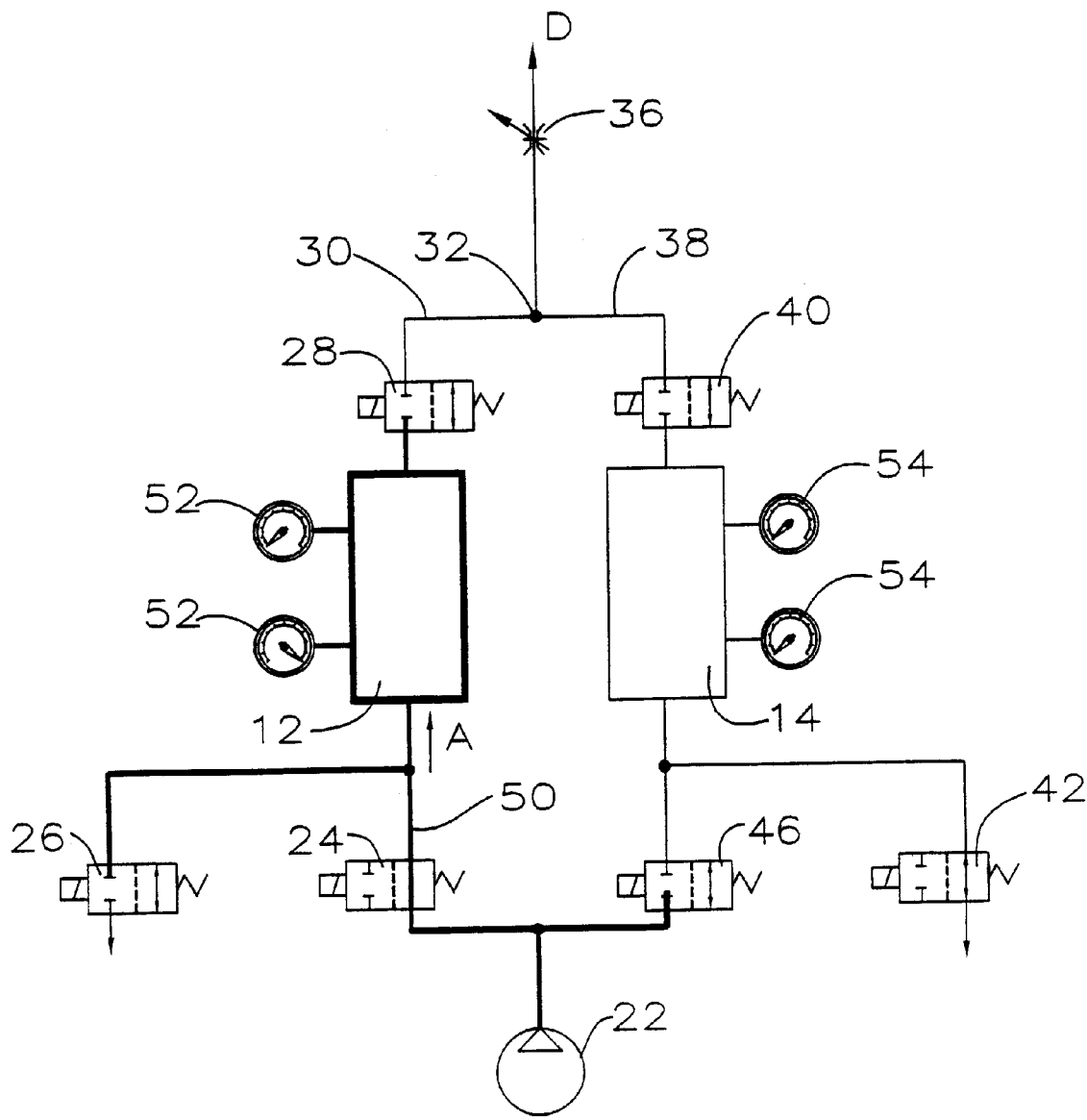
FIG. 4 is a block diagram of a further embodiment of the oxygen concentrator of the present invention during pressurization of a first molecular sieve bed during an initial pressurization phase.
Figure 5:
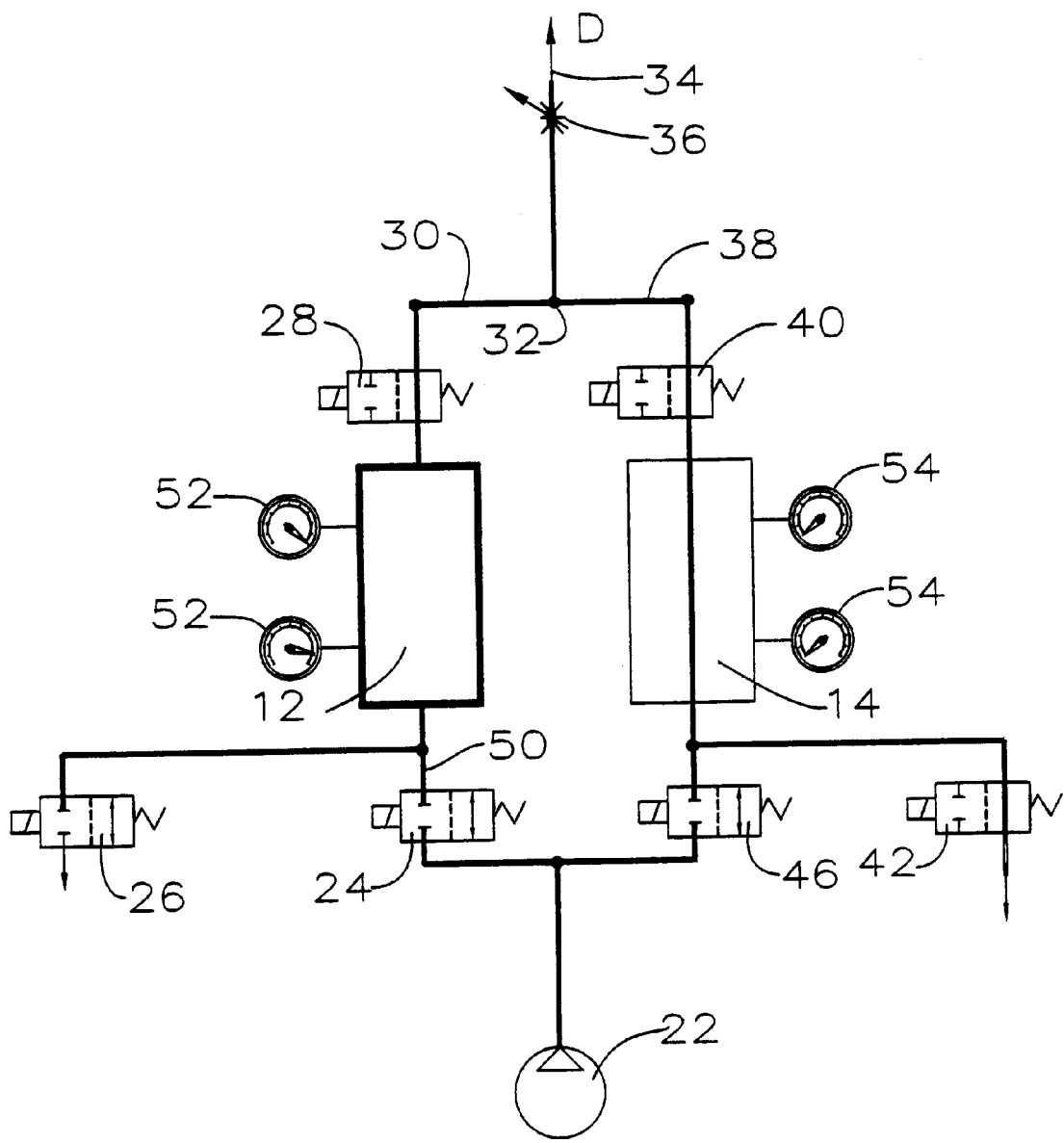
FIG. 5 is a block diagram of the oxygen concentrator of FIG. 4 during an air packet transfer phase.
Figure 6:
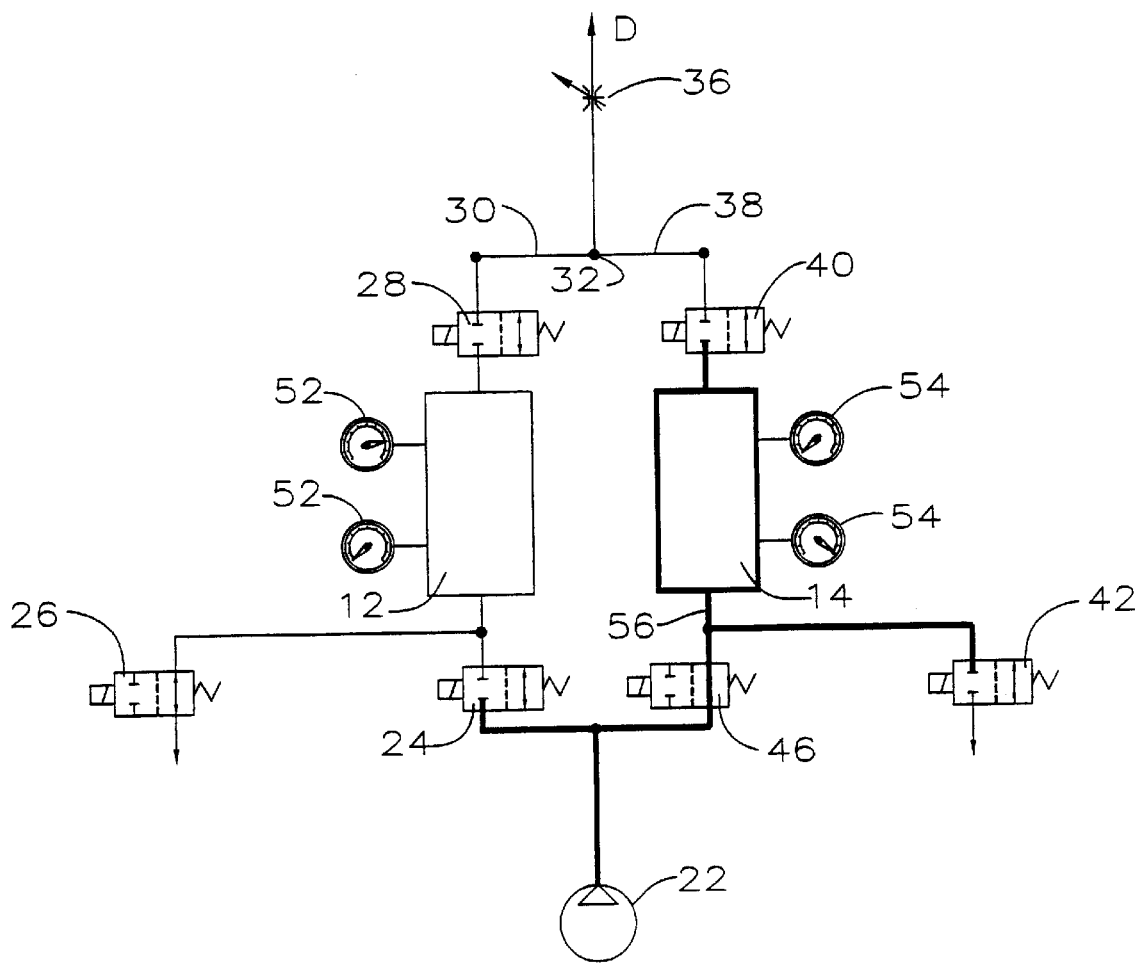
FIG. 6 is the oxygen concentrator of FIG. 5 during pressurization of a second molecular sieve bed.

The steps in concentrating oxygen are illustrated diagrammatically in FIGS. 4–6. The first step is to introduce ambient air into the inside of bed 12 (i.e. a chamber filled with Zeolite), then to pressurize bed 12.

Figure 1A:
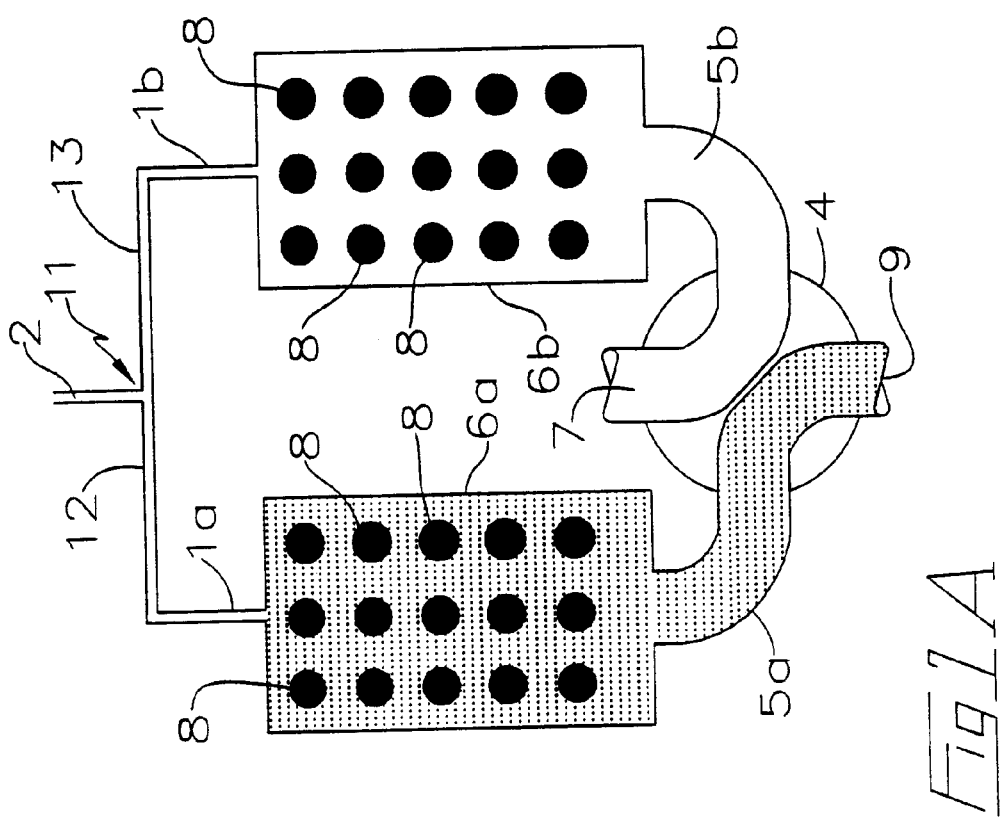

FIG. 4 illustrates pressurizing bed 12 for the first time. Herein the thickened and darkened air supply lines 50 and the darkened bed 12 indicate pressurized flow or pressurized static gas. The control valve 28, nitrogen vent bed 26 and supply valve 46 for bed 14 are closed, while supply valve 24 is open. At this point compressor 22 is introducing ambient air into bed 12 and pressurizing it. This continues until the bed reaches for example 10 psi as indicated by the pressure gauge 52. Next, supply valve 24 is closed and the pressurized air contained in bed 12 is separated into oxygen and nitrogen by the granular Zeolite molecular sieve material 48 better seen in FIG. 1a. At a molecular level the nitrogen is adsorbed by the Zeolite and held as long as the bed is under pressure. This leaves the oxygen-enriched gas within the pressurized chamber or cavity of the bed. It has been observed that this process occurs almost instantaneously. The pressure in bed 14 remains at ambient as indicated by pressure gauge 54.

Next, as shown in FIG. 5, control valve 28 is opened. The oxygen which had been separated within the chamber of bed 12 is the first gas to leave bed 12 as pressure is released through control valve 28. This oxygen-enriched air is fed from bed 12 into bed 14 through conduits 30 and 38. During this transfer some of the oxygen-enriched air is also released via splitter 32 through conduit 34 to the end-use or end-user as air flow in direction D, as regulated by adjustable needle valve 36. Splitter 32 and valve 36 may be a T-junction having a needle valve allowing for control of the split-off flow rate. As better described below, this may also be accomplished by a calibrated orifice controlling the split-off flow rate. As the oxygen-enriched air enters bed 14 it displaces the ambient air in bed 14 out of nitrogen vent 42. A net increase in the oxygen concentration contained within bed 14 results. The counter-flow is discontinued before nitrogen is entered into the system to prevent a drop in oxygen concentration. For example, a bed initially pressurized to 20 psi, counter-flow would be discontinued as the pressure drops to approximately 7 psi because nitrogen will start leaching into the air-stream at that point. In a larger industrial embodiment of the present invention, where the packet system of the present invention is employed for use with large beds, then oxygen or nitrogen sensors may be employed to detect when optimal oxygen concentration levels are reached (i.e. peaked) or to detect when nitrogen levels start to rise so as to control the counter-flow duration. Such sensors may be installed for example adjacent the control valves, for example control valves 28, 40.

The process then repeats, but in the reverse order. As seen in FIG. 6, which shows the pressurization of bed 14, the oxygen-enriched air which had been introduced into bed 14 is contained by closing control valve 40 and nitrogen vent 42. Next, supply valve 46 is opened and compressor 22 begins to compress the oxygen-enriched air, again up to for example 10 psi through air conduits 56 into bed 14. Also, at this time control valve 28 and nitrogen vent 26 are opened to vent off the residual nitrogen from bed 12. Supply valve 24 is closed.

After the molecular sieve material 48 and gas contained within bed 14 are pressurized, control valve 40, control valve 28 and nitrogen vent 26 are opened. The oxygen-enriched air is then passed back into bed 12 from bed 14. As this air is introduced into bed 12 it assists in displacing the residual nitrogen from bed 12 out from nitrogen vent 26.

After an optimized time, nitrogen vent valve 26 is closed along with control valve 28, and supply valve 24 is opened to start the cycle over again from the beginning.

The process of transferring or shunting oxygen-enriched air from one bed to another is known as counter-flow. A reservoir 58 mounted upstream of the inlet for each molecular sieve bed may be employed to increase the counter flow volume to volume-to-the-end-user gas flow ratio.

Figure 6A:
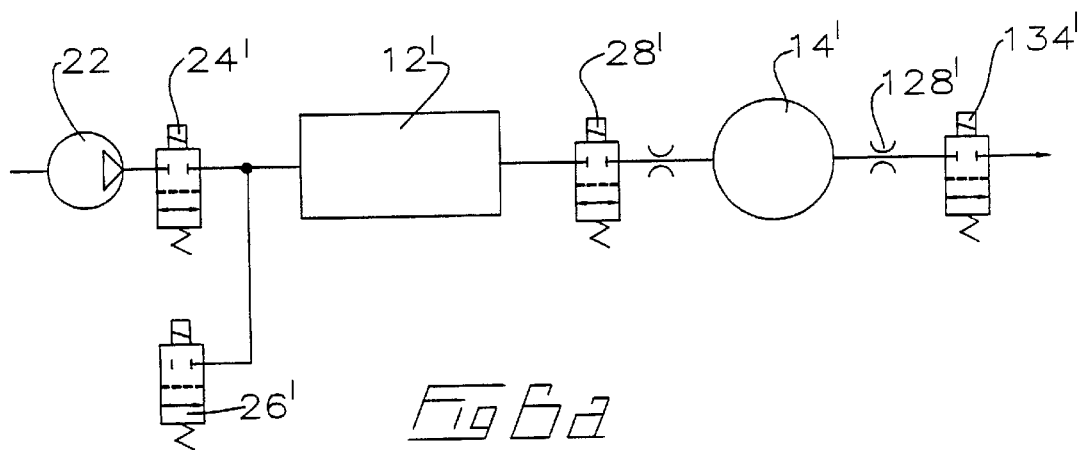
FIG. 6a is a block diagram of one embodiment of the oxygen concentrator of the present invention.

Alternatively as seen in FIG. 6a counterflow may be accomplished by use of only one molecular sieve bed 12' and one reservoir 14'. Compressor 22 pressurizes an air flow through valve 24' into bed 12'. Oxygen-enriched air is shunted through valve 28' from bed 12' into reservoir 14' instead of into a second bed, and then counter-flowed from the reservoir back into the bed using the packet air-flow system of the present invention. This also accomplishes incremental increases per cycle in the oxygen concentration of the air packet being shunted back and forth from and to the bed so as to allow splitting or bleeding off to an end user of an oxygen-enriched air supply through orifice 128' and valve 134'. Nitrogen in bed 12' is purged or vented through valve 26'. Alternatively the oxygen concentration according to the present invention may be accomplished by using a plurality of molecular sieve beds.

The counter-flow process is optimally timed to achieve an incremental increase in oxygen concentration per cycle. One way this is accomplished is by placing an oxygen concentration sensor on the end-user air flow conduit 34 and then, for example using an adjustable or otherwise regulatable splitter 32 to vary the percentage of air flow being diverted in direction D to the end-user and monitoring the percentage oxygen concentration in conduit 34. It has been applicant's experience that in this fashion a maximum percentage oxygen concentration passing through conduit 34 may be ascertained, and once found, the setting of splitter 32 has been correspondingly optimized. Once, for a particular arrangement, an optimized flow rate or valve setting has been ascertained, splitter 32 may be replaced with a non-adjustable flow splitter having a flow restrictor in the end-user gas flow line which is preset or pre-sized to replicate the optimized end-user gas flow rate. Applicant has found it advantageous when optimizing the counter-flow to start with excess counter-flow and then reduce the amount of counter-flow (decreasing the counter-flow time), for example starting with a counter-flow time equivalent to 75% of the time it takes to pressurize the beds to 10 psi. This is not to be taken, however, as implying that pressurization may only be done using a time-based method, as it is intended that the scope of this invention include using an air packet method which is pressure-based rather than time-based. That is, rather than pressurizing or depressurizing the beds for a preset time, it may be that the bed pressure is monitored and the air packet shunted upon a pre-set pressure threshold being met. Applicant has also found that using the method of the present invention, the size of the molecular sieve beds may be reduced from that presently found in the prior art, for example reduced to 75% of the size currently used in the prior art. Applicant has also found that using the method and apparatus of the present invention, that oxygen levels in the end-user gas flow line may reach in excess of 90%, with 95% oxygen levels thought to be sustainably available.

Figure 7:
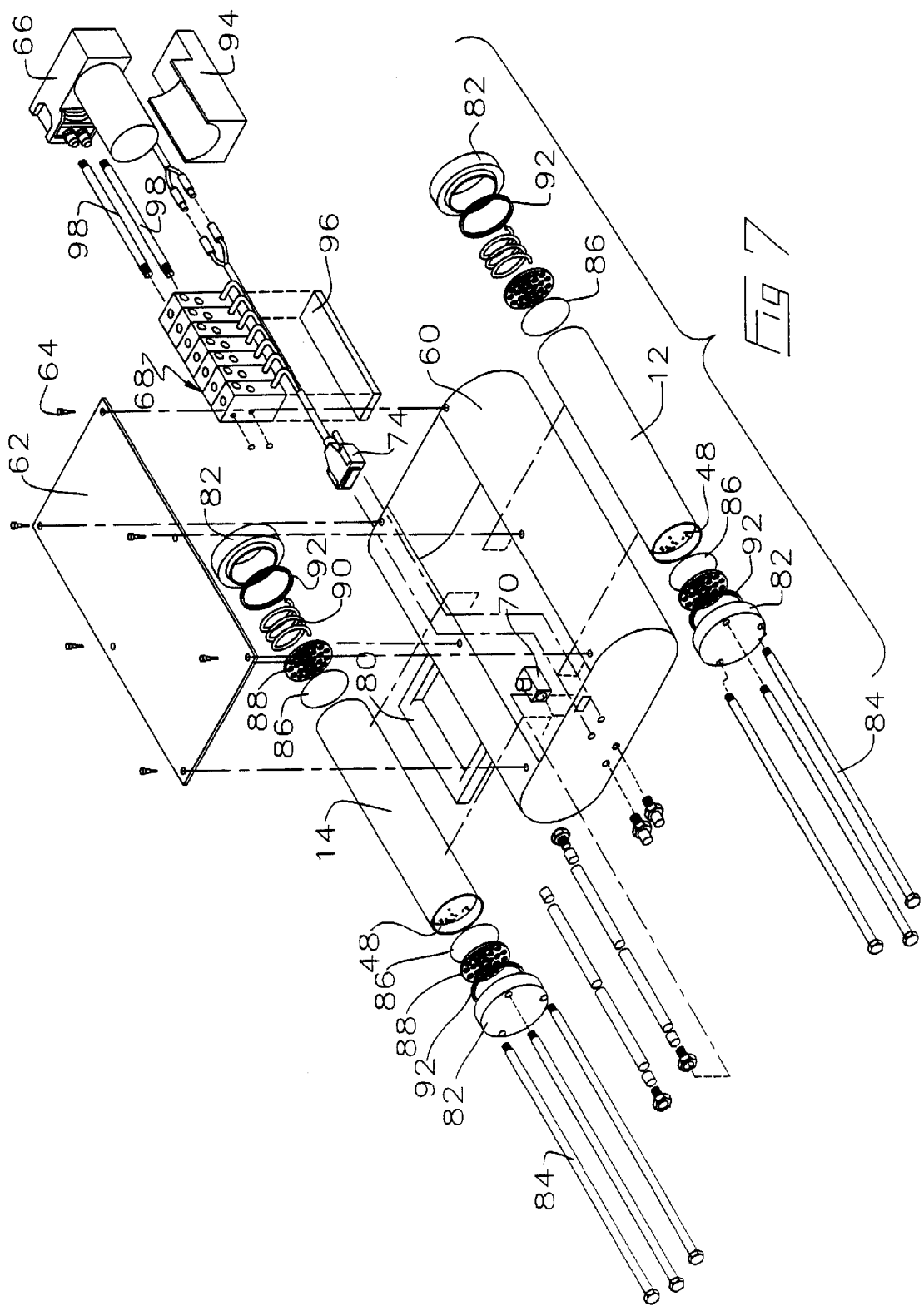
FIG. 7 is, in exploded perspective view, one embodiment of the oxygen concentrator of the present invention.

As seen in the embodiment of FIG. 7, molecular sieve beds 12 and 14 are contained within housing 60 in parallel spaced apart array so as to dispose the beds displaced laterally within the housing cavity thereby leaving a space between the beds running the length of the housing. This space between the beds may be accessed in one embodiment by removal of face plate 62 from housing 60, face plate 62 being releasably mounted to housing 60 for example by means of screw fasteners 64.

Figure 8:
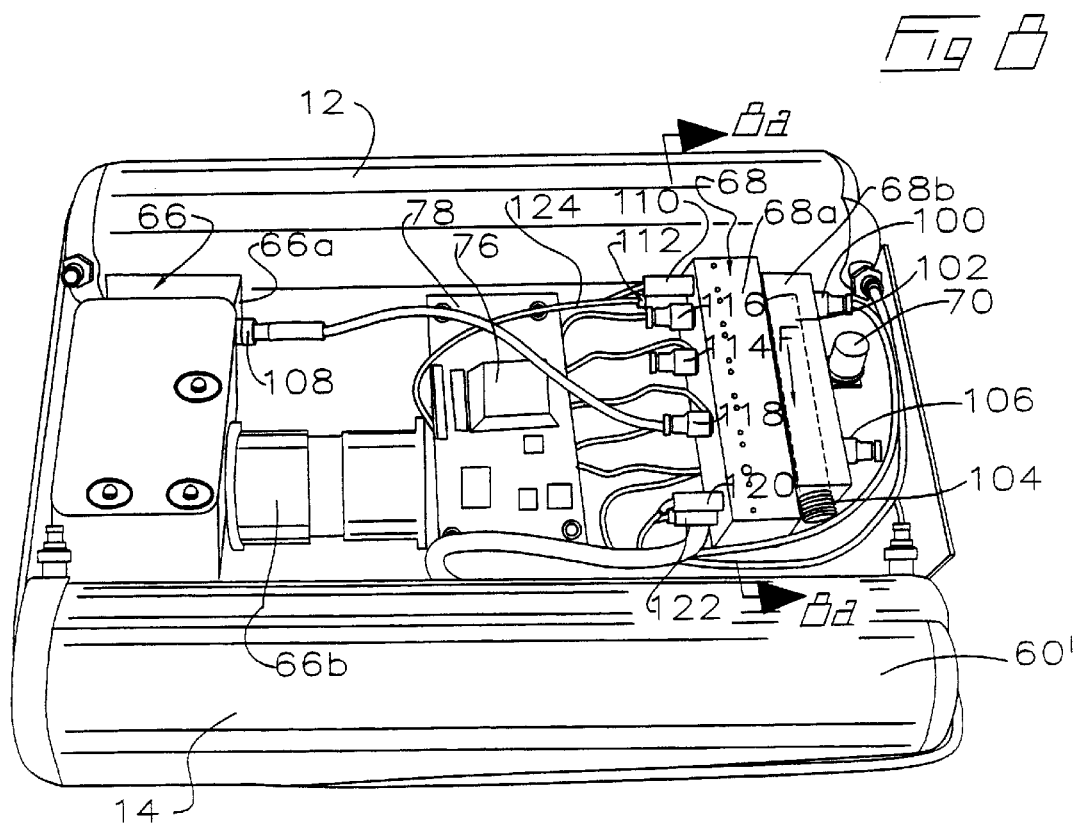
FIG. 8 is, in perspective view, a further embodiment of the oxygen concentrator of the present invention.

Mounted between beds 12 and 14 within housing 60 are a compressor 66, a valve and manifold housing 68, a splitter valve 70 (to serve the function of splitter 32) and various flexible pipe or tubing to serve as the air conduits as better described below. The actuation timing of the valve actuation and the actuation timing of the compressor are controlled by signals from a PLC or other processor. In the embodiment of FIG. 7, the processor is remote from housing 60 and communicates via interface plug 74. In the embodiment of FIG. 8, which is otherwise substantially similar to that of FIG. 7, the remote PLC or processor is replaced with an onboard PLC or processor 76 mounted on circuit board 78, where circuit board 78 is mounted between compressor 66 and valve housing 68. Also, in the embodiment of FIG. 8, faceplate 62 is replaced with a one-half clam shell style cover (not shown), that is, the housing is formed as a clam shell cover arrangement as better seen in FIG. 9 and labeled as housing 60'. An end-mounted control panel may contain an on/off power switch 63, an air extraction port 34' a perforated air intake plate or grate 65, and a 12 volt DC connector 67.

Housing 60' may have a handle 80 mounted along one lateral side for carrying of the oxygen concentrator of the present invention, it being understood that providing for hand-held carrying is not intended to be limiting. The present invention is also intended in alternative embodiments to be worn by a user, for example in or as a backpack or hip pack or so-called fanny pack 81 such as seen in FIG. 10. Conduit 34 extends from the housing to the end-user so that, where the end-user is a patient requiring a supply of oxygen-enriched air, conduit 34 may supply nasal tubes 35 as commonly in use in the prior art.

In the embodiments of FIGS. 7 and 8, beds 12 and 14 may be 2 inch inside diameter pipe, having a length of approximately 12 inches so as to provide for carrying therein molecular sieve material having a length of, in one embodiment, at least 9 and ½ inches in order to obtain oxygen concentrations of greater than 90 per cent. The beds are sealed on their ends by end caps 82, suitably bored or otherwise ported so as to cooperate with air conduit tubing forming the pneumatic circuit (not shown in FIG. 7 for clarity) and to allow for the fastening of the end caps onto the ends of the bed pipes for example by the use of elongate bolts 84 as seen in FIG. 7. The Zeolite molecular sieve material 48 is sandwiched longitudinally within the cylindrical pipe housing of each bed between a pair of porous membranes 86, themselves sandwiched between a pair of porous backing plates 88. The sandwich of porous backing plates 88, porous membranes 86, and molecular sieve material 48 may be resiliently urged to one end of the bed by a resilient biasing means such as helical spring 90. The porous membranes 86, which may be felt porous backing material or other material to contain material of molecular sieve bed from passing through the openings of porous backing plates 88, sized to cover the entire opening within the cylindrical beds. Porous backing plates 88 may be rigid plates having holes drilled therethrough. The end caps 82 may be sealed onto the ends of the piping forming the bed housings by means of O-rings 92.

Compressor 66, which may be a Thomas™ 8009DC compressor having its mounting plate removed and adapted to rotate the head ports by 180 degrees, or a Thomas™ 7006 series compressor as depicted in FIG. 8, may be mounted into housing 60 by means of a resilient mounting plate 94 which may be of open cell high density foam or Sorbothane™ or other dampening material. A further resilient mounting plate 96, which may also be of open cell high density foam may be employed to mount valve housing 68 into housing 60. In the embodiment of FIG. 7, valve and manifold housing 68 includes a series of 7 Humphrey™ 310 series 24 volt DC stand-alone valves bolted into side-by-side adjacent array by means of elongate bolts 98. As depicted in FIG. 8, the valves may also be Humphrey™ HK5 valves.

Valve and manifold housing 68 has an array of valves mounted adjacently as a block 68a, and conveniently disposed along the back side of the block is a reservoir and muffler manifold 68b. Air conduits lead into the muffler cavity, which may be a bore formed in manifold 68b and filled with sound-dampening material, for example cellulose fibre, and a conduit leads from the muffler to the compressor so as to supply air to the compressor. Further conduit then leads from the compressor into the valve block 68a so as to supply compressed air to the supply valves. Thus as seen in FIG. 8, coupler 100 and its corresponding air conduit draw air from outside of the housing and feed it into muffler 102 shown in dotted outline. Muffler 102 may be accessed through end cap 104, which may be threadably mounted into the end of the muffler bore. Air from the air intake coupler 100 passes through muffler 102 in direction F so as to exit through the muffler output coupler 106 and its corresponding air conduit which feeds air into compressor 66, and in particular, into the compressor cylinder head 66a. Upon compression of the air by the operation of the compressor cylinder contained within the compressor cylinder head housing 66a by the operation of motor 66b, air is compressed and output through compressor output coupler 108 and its corresponding air conduit.

Figure 8A:
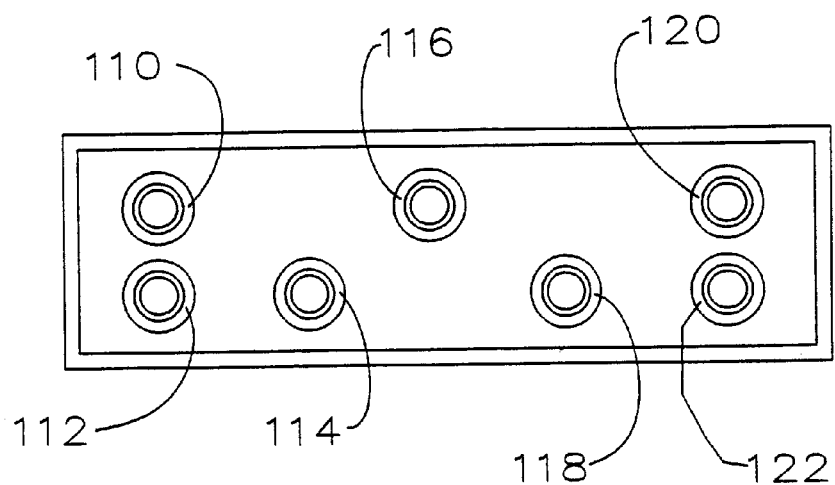
FIG. 8a is a cross-sectional view along line 8a–8a in FIG. 8.
Figure 4:
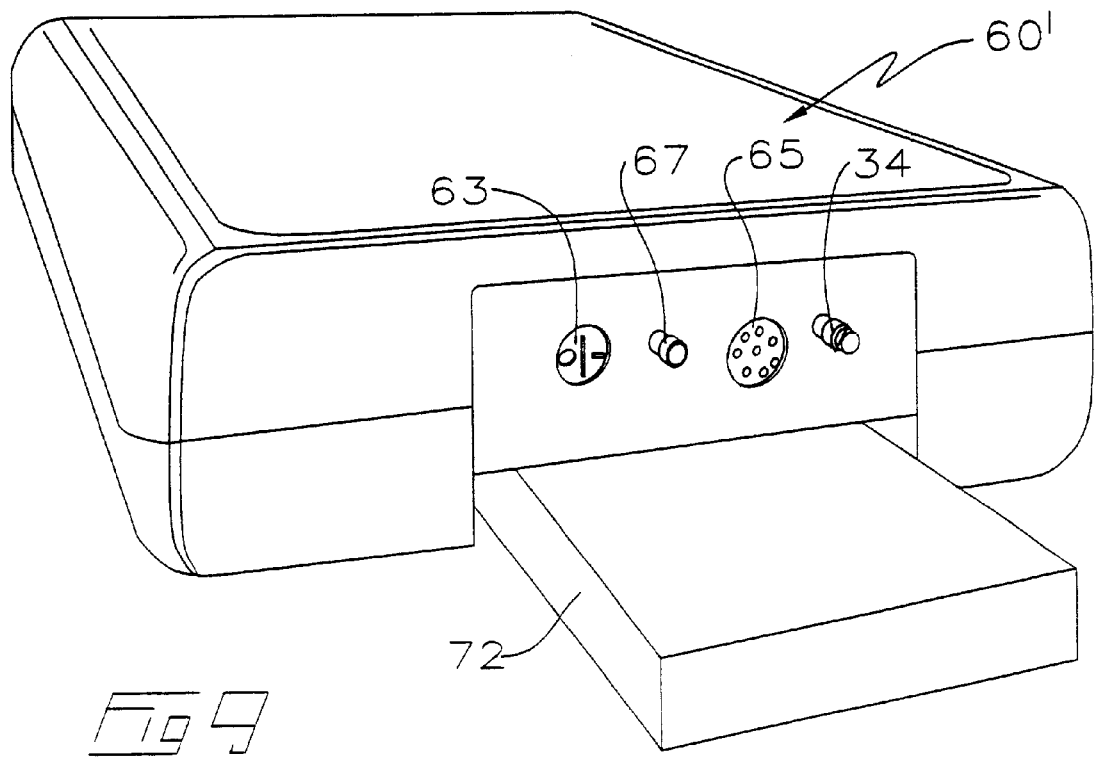
Figure 11:
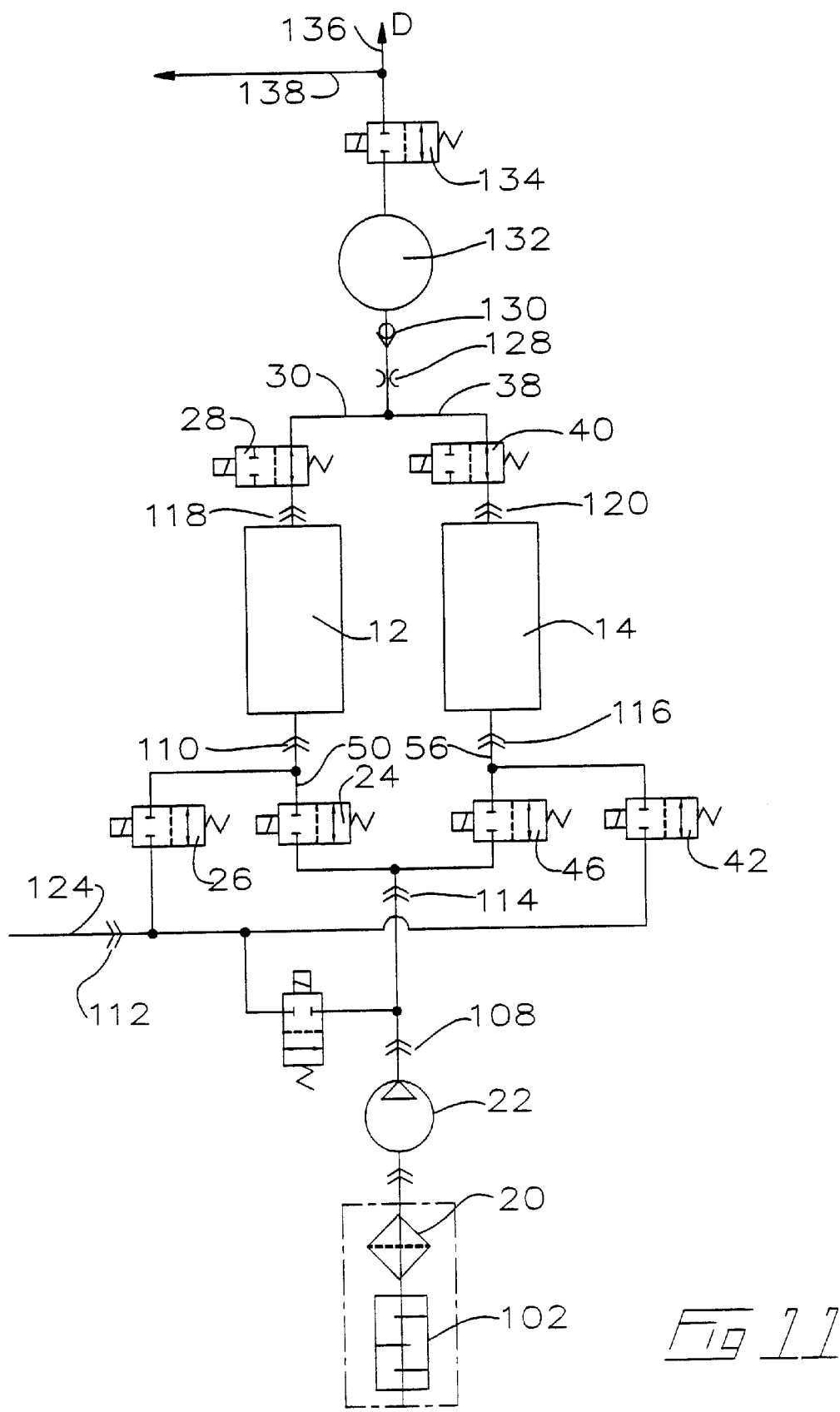
FIG. 11 is a block diagram of a further embodiment of the oxygen concentrator according to the present invention.
Figure 12:
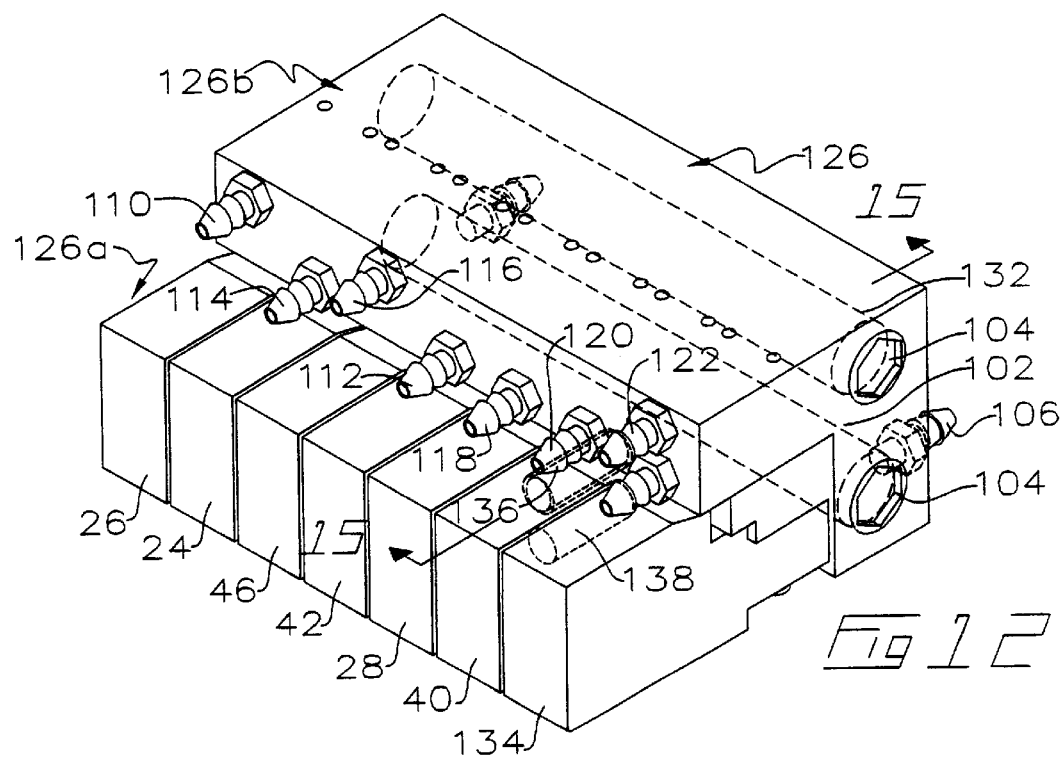
FIG. 12 is, in perspective view, a valve and manifold housing according to one embodiment of the oxygen concentrator of the present invention.
Figure 13:
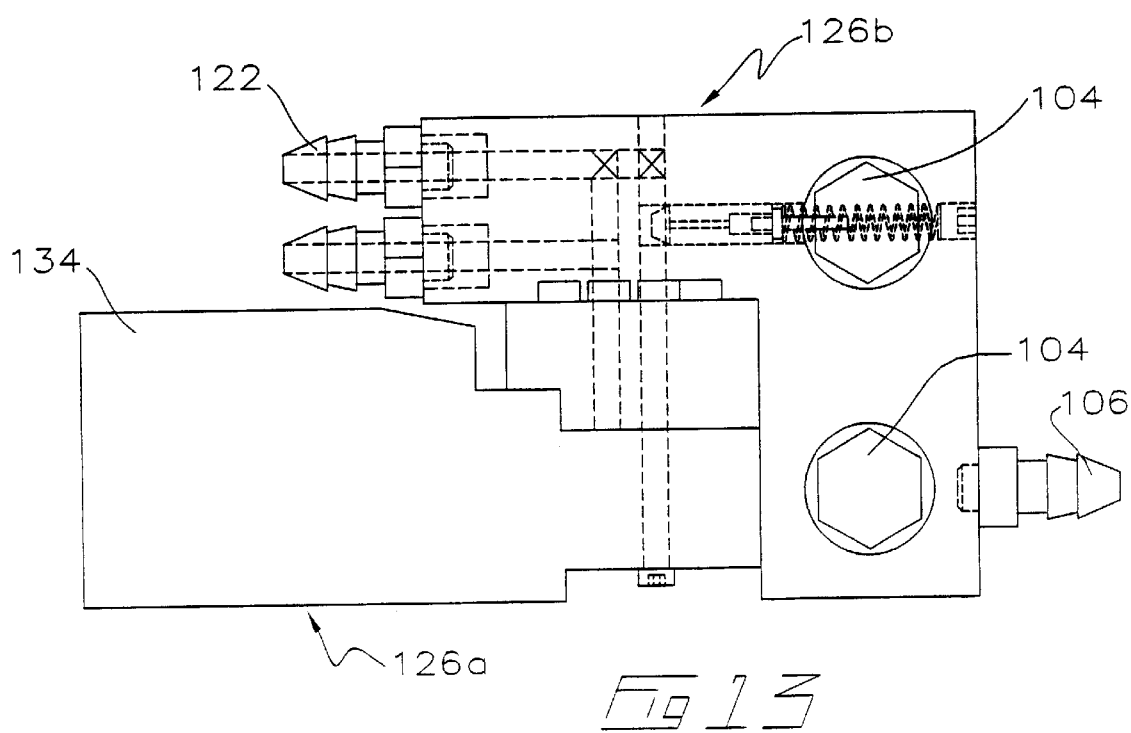
FIG. 13 is, in side elevation view, the valve and manifold housing of FIG. 12.
Figure 14:
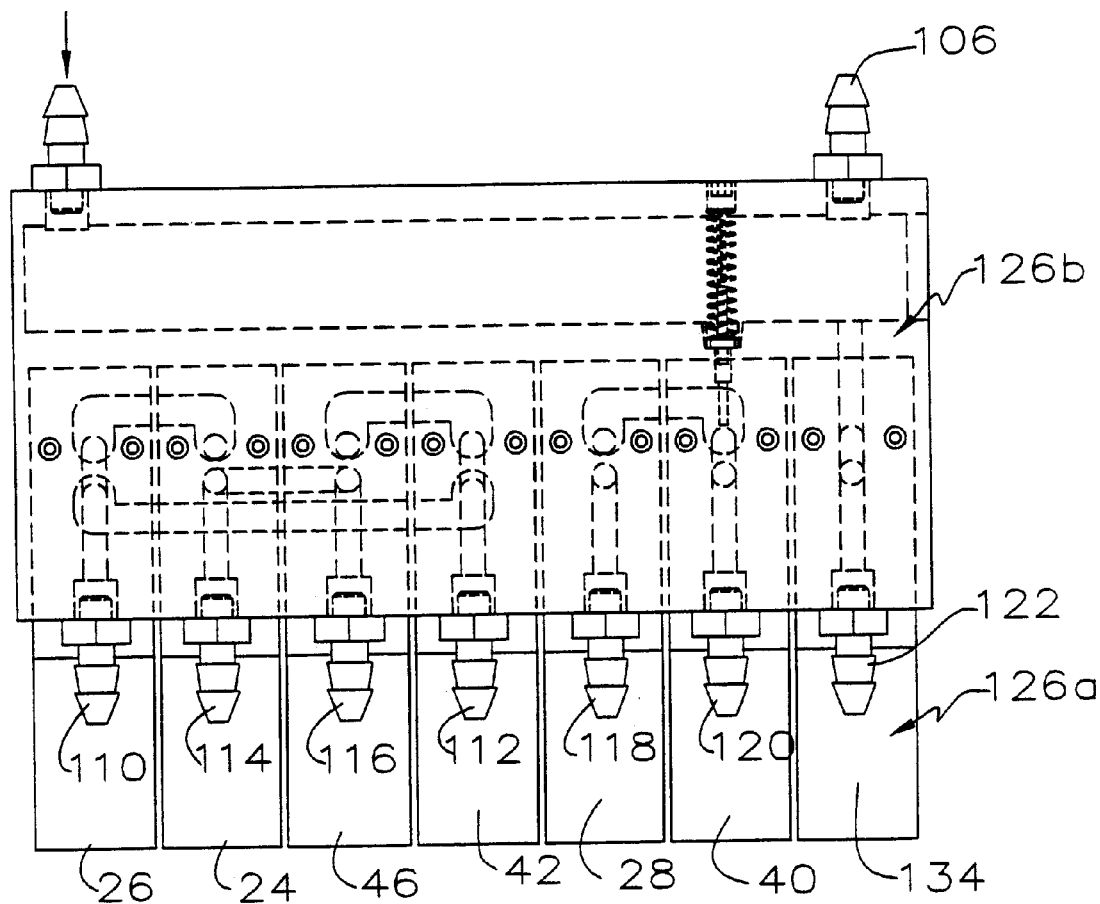
FIG. 14 is, in plan view, the valve and manifold housing of FIG. 13.
Figure 15:
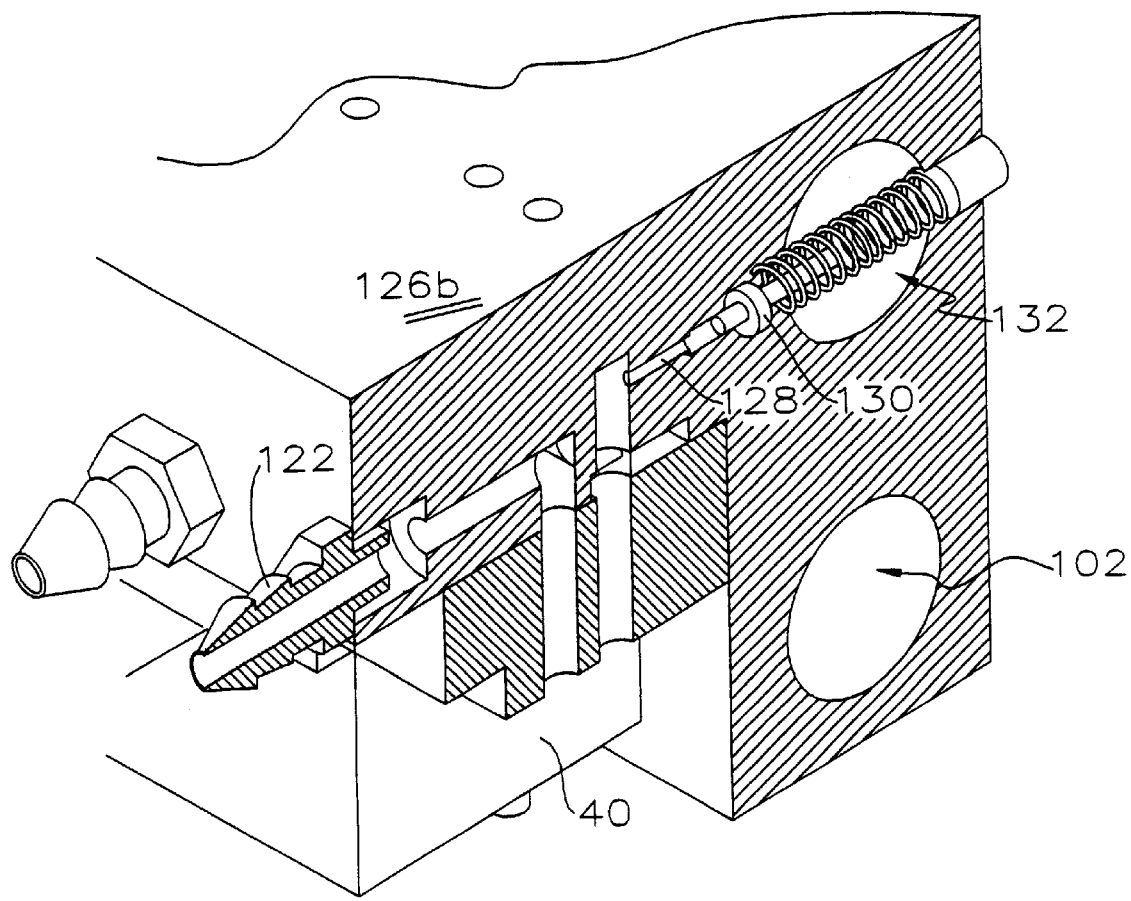
FIG. 15 is a cross-sectional view along line 15—15 in FIG. 12.

As better seen in FIG. 8a, which illustrates the front face of valve block 68a, seven air conduit couplers are provided. Without intending to be limiting in their arrangement, they are the bed 12 infeed coupler 110 between supply valve 24 and bed 12, the common nitrogen vent coupler 112 which commonly vents from both nitrogen vent 26 and nitrogen vent 42, the compressed air infeed coupler 114 from compressor 22, the bed 14 infeed coupler 116 between bed 14 and supply valve 46, the bed 12 outfeed coupler 118 between bed 12 and control valve 28, bed 14 outfeed coupler 120 between bed 14 and control valve 40, and the patient air flow coupler 122. These couplers are illustrated in the diagram of FIG. 11 which also illustrates the common venting of nitrogen vents 26 and 42 through vent line 124 and the removal of the pressure relief valve of FIG. 3 as being unnecessary due to the switching on and off of compressor 22. FIG. 11 also illustrates features of an alternative embodiment for valve and manifold housing 68, and in particular valve and manifold housing 126 as illustrated in FIGS. 12–16.

FIG. 11 also illustrates a further embodiment of the oxygen concentrator of the present invention. Rather than using an adjustable flow splitter 32 or an adjustable needle valve 36, the proportion of oxygen-enriched air flow flowing in direction D through conduit 34 is regulated by a pre-set optimized orifice 128 which then flows through a check valve 130 into reservoir 132. Outflow from reservoir 132 is controlled by demand valve 134. The air flow then may split between air flow to the patient along conduit 136 and air flow to a pressure sensor (not shown) along conduit 138. The sensor on conduit 138 may then be employed to sense when a patient is demanding a surge release of oxygen-enriched air from reservoir 132. Thus when the patient creates a drop in pressure in conduit 136 such as would be caused by suction applied to conduit 136, the sensor detects the drop in pressure below a pre-set threshold and causes the processor to trigger the release of the reserve of oxygen-enriched air contained within reservoir 132. In alternative embodiments, the reservoir may be large enough to contain a sufficient supply of oxygen-enriched air for more than one inhalation on demand by the patient through demand valve 134.

This embodiment is reflected also in FIGS. 12–16 which illustrate a bored reservoir 132 bored into the manifold block 126b parallel to muffler 102. As with the muffler, the reservoir may be bored and sealed using a threaded end cap 104.

As seen in FIGS. 16 and 16a, it is intended to form part of the scope of the present invention that the molecular sieve beds 12" and 14" may be curved rather than linear. For example, the beds 12" and 14" may be curved along their length so as to better conformally fit about the waist of a user wearing them such as in FIG. 10. End plates 69 may be bolted through bolt holes 71 to the frame or casing of the housing or beds respectively to seal the ends of the beds. The beds may be formed as a curved adjacent parallel pair of beds such as seen in FIG. 16 or, consistent with the previously described embodiments, be laterally spaced apart and parallel within a housing which would also then have a correspondingly curved surface to facilitate ease and comfort of wearing the oxygen concentrator of the present invention. In all such wearable embodiments, it may be that battery 72, control switches such as the "on/off" switch, the air intake, the end-user air flow outlet and the like are mounted within the carrying media, such as a back pack, fanny pack etc., so as to be exposed from one end of the housing and from one side of the carrying media. Thus as seen in FIG. 10 the user has ease of access to the control functions and to the air flow outlet from which the air flow conduit extends for use.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. In an oxygen concentrator including:
   an air compressor,
   an air-tight first container in fluid communication with said compressor, through a first gas conduit, an air-tight second container in fluid communication with said first container through a second gas conduit,
   wherein said first container contains a molecular sieve bed,
   a gas flow controller controlling actuation of valves mounted to said gas conduits,
   a gas flow splitter mounted to said second gas conduit for diverting a portion of said packet of incrementally oxygen-enriched air into a gas line for delivery of oxygen-enriched air to an end use downstream along said gas line,
   said valves regulating air flow through said conduits, a method of oxygen enrichment comprising the sequential steps, in repeating cycles, of:
   (a) preventing gas flow between said first and second containers and allowing compressed gas from said compressor into said first container during a first gas pressurization phase, whereby said first container is pressurized to a threshold pressure level to create a packet of incrementally oxygen-enriched air;
   (b) preventing gas flow into said first container from said compressor and allowing gas flow from said first container into said second container during an air packet transfer phase, wherein said packet of incrementally oxygen-enriched air is transferred to said second container;
   (c) preventing gas flow into said second container from said first container and allowing gas to vent to atmosphere out from said first container through a vent valve of said first container;
   (d) allowing gas flow between said first and second containers from said second container into said first container during an air packet counter-flow phase, wherein said packet of incrementally oxygen-enriched air flows from said second container to said first container; and,
   (e) preventing gas flow venting from said first container through said vent valve of said first container.

2. The method of claim 1, wherein said oxygen concentrator further includes a molecular sieve bed in said second container and wherein said second container is in fluid communication with said compressor through a third conduit, further comprising the steps of:
   (a) following said air packet transfer phase and following preventing gas flow into said second container from said first container, said gas flow controller allowing compressed gas from said compressor into said second container during a second gas pressurization phase, whereby said second container is pressurized to said threshold pressure level; and
   (b) following preventing said gas flow from venting from said first container through said vent valve of said first container and following preventing gas flow between said first and second containers during said first gas pressurization phase, said gas flow controller allowing gas to vent to atmosphere out from said second container through a vent valve of said second container and preventing gas flow into said second container from said compressor.

3. The method of claim 2 wherein said gas flow controller is a processor cooperating with said compressor, further comprising the step of shutting off said compressor while gas flow from said compressor into both said first and second containers is prevented.

4. In a gas concentrator for enriching a target component gas concentration and minimizing a waste component gas concentration in a gas flow including:
   an air compressor,
   an air-tight first container in fluid communication with said compressor, through a first gas conduit, an air-tight second container in fluid communication with said first container through a second gas conduit,
   wherein said first container contains a molecular sieve bed for adsorbing a waste component gas,
   a gas flow controller controlling actuation of valves mounted to said gas conduits,
   a gas flow splitter mounted to said second gas conduit for diverting a portion of said gas packet into a gas line for delivery of target component gas-enriched air to an end use downstream along said gas line,
   said valves regulating air flow through said conduits, a method of oxygen enrichment comprising the sequential steps, in repeating cycles, of:
   (a) preventing gas flow between said first and second containers and allowing compressed gas from said compressor into said first container during a first gas pressurization phase, whereby said first container is pressurized to a threshold pressure level to create a gas packet having incrementally enriched target component gas concentration;

(b) preventing gas flow into said first container from said compressor and allowing gas flow from said first container into said second container during an air packet transfer phase, wherein said gas packet is transferred to said second container;

(c) preventing gas flow into said second container from said first container and allowing gas to vent to atmosphere out from said first container through a vent valve of said first container;

(d) allowing gas flow between said first and second containers from said second container into said first container during an air packet counter-flow phase, wherein said gas packet flows from said second container to said first container; and, (e) preventing gas flow venting from said first container through said vent valve of said first container.

5. The method of claim 4, wherein said gas concentrator further includes a molecular sieve bed in said second container and wherein said second container is in fluid communication with said compressor through a third conduit, further comprising the steps of:

(a) following said air packet transfer phase and following preventing gas flow into said second container from said first container, said gas flow controller allowing compressed gas from said compressor into said second container during a second gas pressurization phase, whereby said second container is pressurized to said threshold pressure level; and (b) following preventing said gas flow from venting from said first container through said vent valve of said first container and following preventing gas flow between said first and second containers during said first gas pressurization phase, said gas flow controller allowing gas to vent to atmosphere out from said second container through a vent valve of said second container and preventing gas flow into said second container from said compressor.

6. The method of claim 5 wherein said gas flow controller is a processor cooperating with said compressor, further comprising the step of shutting off said compressor while gas flow from said compressor into both said first and second containers is prevented.

7. An oxygen concentrator for enriching an oxygen gas concentration and minimizing a nitrogen gas concentration in a gas flow comprising:

an air compressor, an air-tight first container in fluid communication with said compressor, through a first gas conduit, an air-tight second container in fluid communication with said first container through a second gas conduit, wherein said first container contains a molecular sieve bed for adsorbing nitrogen, a gas flow controller controlling actuation of valves mounted to said gas conduits, said valves regulating air flow through said conduits so as to sequentially, in repeating cycles:

(a) prevent gas flow between said first and second containers and to allow compressed gas from said compressor into said first container during a first gas pressurization phase, whereby said first container is pressurized to a threshold pressure level to create a packet of incrementally oxygen-enriched air;

(b) prevent gas flow into said first container from said compressor and allow gas flow from said first container into said second container during an air packet transfer phase, wherein said packet of incrementally oxygen-enriched air is transferred to said second container;

(c) prevent gas flow into said second container from said first container and allow gas to vent to atmosphere out from said first container through a vent valve of said first container;

(d) allow gas flow between said first and second containers from said second container into said first container during an air packet counter-flow phase, wherein said packet of incrementally oxygen-enriched air flows from said second container to said first container; and, (e) prevent gas flow venting from said first container through said vent valve of said first container, a gas flow splitter mounted to said second gas conduit for diverting a portion of said packet of incrementally oxygen-enriched air into a gas line for delivery of oxygen-enriched air for an end use downstream along said gas line, wherein both said first and second containers contain molecular sieve beds and wherein said second container is in fluid communication with said compressor through a third conduit, and wherein said gas flow controller, following said air packet transfer phase and following preventing gas flow into said second container from said first container, allows compressed gas from said compressor into said second container during a second gas pressurization phase, whereby said second container is pressurized to said threshold pressure level, and wherein said gas flow controller, following preventing said gas flow from venting from said first container through said vent valve of said first container and following preventing gas flow between said first and second containers during said first gas pressurization phase, allows gas to vent to atmosphere out from said second container through a vent valve of said second container and prevents gas flow into said second container from said compressor, and wherein said gas flow controller is a processor cooperating with said compressor so as to shut off said compressor when gas flow from said compressor into both said first and second containers is prevented, and wherein both said processor and said compressor are battery powered by a battery, and wherein said first and second containers, said conduits, said valves, said processor, said compressor and said battery are mounted in a housing.

8. The device of claim 7 wherein said first and second containers are elongate hollow conduits and wherein said molecular sieve beds are Zeolite and wherein said first and second containers are generally parallel and mounted in said housing in parallel array.

9. The device of claim 8 wherein said array is spaced apart laterally relative to the length of said containers so as to define a channel therebetween.

10. The device of claim 9 wherein said processor and said compressor are mounted in said channel.

11. The device of claim 10 further comprising a valve and manifold housing mounted in said channel, said valves mounted to said valve and manifold housing, said valve and manifold housing having interconnecting manifolds for interconnecting said valves to said first and second containers and said compressor via said gas conduits.

12. The device of claim 11 further comprising a gas reservoir in fluid communication with said gas flow splitter, said reservoir for containing a reserve of said oxygen-enriched air for delivery to said end use, and wherein one of said valves is a demand valve cooperating between said gas line and said reservoir for release of said reserve into said gas line upon a triggering event triggering actuation of said demand valve.

13. The device of claim 12 further comprising a pressure sensor cooperating with said gas line, wherein said triggering event is a drop in pressure in said gas line sensed by said pressure sensor, wherein said pressure sensor provides a triggering signal to trigger said actuation of said demand valve upon detecting said drop in pressure.

14. The device of claim 13 wherein said drop in pressure is to a pre-set lower threshold pressure, below which said pressure sensor provides said triggering signal.

15. The device of claim 14 wherein said compressor is run intermittently upon actuation signals from said processor so as to only run when required.

16. The device of claim 7 wherein said end use is oxygen supply to an end user, and wherein said first and second containers are elongate and curved along their length so as to conform to a body shape of said end user when said oxygen concentrator is worn by said end user.

17. The device of claim 7 wherein said end use is oxygen supply to an end user, and wherein said first and second containers are elongate and curved along their length so as to conform to a body shape of said end user when said oxygen concentrator is worn by said end user.

18. The device of claim 7 wherein said end use is oxygen supply to an end user and wherein said oxygen concentrator is adapted to be worn by said end user.

19. A gas concentrator for enriching a target component gas concentration and minimizing a waste component gas concentration in a gas flow comprising:
   an air compressor,
   an air-tight first container in fluid communication with said compressor, through a first gas conduit, an air-tight second container in fluid communication with said first container through a second gas conduit,
   wherein said first container contains a molecular sieve bed for adsorbing a waste component gas,
   a gas flow controller controlling actuation of valves mounted to said gas conduits, said valves regulating air flow through said conduits so as to sequentially, in repeating cycles:
      (a) prevent gas flow between said first and second containers and to allow compressed gas from said compressor into said first container during a first gas pressurization phase, whereby said first container is pressurized to a threshold pressure level to create a gas packet having an incrementally enriched target component gas concentration;
      (b) prevent gas flow into said first container from said compressor and allow gas flow from said first container into said second container during an air packet transfer phase, wherein said gas packet is transferred to said second container;
      (c) prevent gas flow into said second container from said first container and allow gas to vent to atmosphere out from said first container through a vent valve of said first container;
      (d) allow gas flow between said first and second containers from said second container into said first container during an air packet counter-flow phase, wherein said gas packet flows from said second container to said first container; and,
      (e) prevent gas flow venting from said first container through said vent valve of said first container,
   a gas flow splitter mounted to said second gas conduit for diverting a portion of said gas packet into a gas line for delivery of target component gas-enriched air for an end use downstream along said gas line,
   wherein both said first and second containers contain molecular sieve beds and wherein said second container is in fluid communication with said compressor through a third conduit,
   and wherein said gas flow controller, following said air packet transfer phase and following preventing gas flow into said second container from said first container, allows compressed gas from said compressor into said second container during a second gas pressurization phase, whereby said second container is pressurized to said threshold pressure level,
   and wherein said gas flow controller, following preventing said gas flow from venting from said first container through said vent valve of said first container and following preventing gas flow between said first and second containers during said first gas pressurization phase, allows gas to vent to atmosphere out from said second container through a vent valve of said second container and prevents gas flow into said second container from said compressor,
   and wherein said gas flow controller is a processor cooperating with said compressor so as to shut off said compressor when gas flow from said compressor into both said first and second containers is prevented, and wherein both said processor and said compressor are battery powered by a battery, and wherein said first and second containers, said conduits, said valves, said processor, said compressor and said battery are mounted in a housing.

20. The device of claim 19 wherein said first and second containers are elongate hollow conduits and wherein said first and second containers are generally parallel and mounted in said housing in parallel array.

21. The device of claim 20 wherein said array is spaced apart laterally relative to the length of said containers so as to define a channel therebetween.

22. The device of claim 21 wherein said processor and said compressor are mounted in said channel.

23. The device of claim 22 further comprising a valve and manifold housing mounted in said channel, said valves mounted to said valve and manifold housing, said valve and manifold housing having interconnecting manifolds for interconnecting said valves to said first and second containers and said compressor via said gas conduits.

24. The device of claim 23 further comprising a gas reservoir in fluid communication with said gas flow splitter, said reservoir for containing a reserve of said target component gas-enriched air for delivery to said end use, and wherein one of said valves is a demand valve cooperating between said gas line and said reservoir for release of said reserve into said gas line upon a triggering event triggering actuation of said demand valve.

25. The device of claim 24 further comprising a pressure sensor cooperating with said gas line, wherein said triggering event is a drop in pressure in said gas line sensed by said pressure sensor, wherein said pressure sensor provides a triggering signal to trigger said actuation of said demand valve upon detecting said drop in pressure.

26. The device of claim 25 wherein said drop in pressure is to a pre-set lower threshold pressure, below which said pressure sensor provides said triggering signal.

27. The device of claim 26 wherein said compressor is run intermittently upon actuation signals from said processor so as to only run when required.

28. The device of claim 19 wherein said end use is oxygen supply to an end user, and wherein said first and second containers are elongate and curved along their length so as to conform to a body shape of said end user when said gas concentrator is worn by said end user.

29. The device of claim 19 wherein said end use is oxygen supply to an end user, and wherein said first and second containers are elongate and curved along their length so as to conform to a body shape of said end user when said oxygen concentrator is worn by said end user.

30. The device of claim 19 wherein said end use is oxygen supply to an end user and wherein said oxygen concentrator is adapted to be worn by said end user.

* * * * *